(12) United States Patent
Reim et al.

(10) Patent No.: US 8,263,577 B2
(45) Date of Patent: Sep. 11, 2012

(54) WATER-SOLUBLE IRON CARBOHYDRATE DERIVATIVE COMPLEXES, THE PREPARATION THEREOF, AND MEDICAMENTS COMPRISING THEM

(75) Inventors: Stefan Reim, St. Gallen (CH); Erik Philipp, Wittenbach (CH); Felix Funk, Winterthur (CH); Hans-Martin Mueller, Engelburg (CH); Peter Geisser, St. Gallen (CH)

(73) Assignee: Vifor (International) AG, St. Gallen (CH)

( * ) Notice: Subject to any disclaimer, the term of this patent is extended or adjusted under 35 U.S.C. 154(b) by 314 days.

(21) Appl. No.: 12/599,343

(22) PCT Filed: May 21, 2008

(86) PCT No.: PCT/EP2008/056276
§ 371 (c)(1),
(2), (4) Date: Nov. 9, 2009

(87) PCT Pub. No.: WO2008/145586
PCT Pub. Date: Dec. 4, 2008

(65) Prior Publication Data
US 2010/0305063 A1 Dec. 2, 2010

(30) Foreign Application Priority Data
May 29, 2007 (EP) .................................... 07109081

(51) Int. Cl.
*A01N 43/04* (2006.01)
*A61K 31/70* (2006.01)
(52) U.S. Cl. ........................................... 514/54; 514/23

(58) Field of Classification Search ........................ None
See application file for complete search history.

(56) References Cited

U.S. PATENT DOCUMENTS

| 2006/0205691 A1 | 9/2006 | Geisser et al. | |
| 2008/0207558 A1* | 8/2008 | Sacchi et al. | 514/53 |
| 2008/0234226 A1* | 9/2008 | Erichsen et al. | 514/59 |

FOREIGN PATENT DOCUMENTS

WO 2006/111802 A1 10/2006

OTHER PUBLICATIONS

"Derivative", Merriam-Webster's Online Dictionary < http://www.merriam-webster.com/dictionary/derivative >, accessed Jan. 6, 2012.*
International Search Report for corresponding PCT/EP2008/056276 mailed Aug. 18, 2008, two pages.
International Preliminary Report on Patentability for corresponding PCT/EP2008/056276 mailed Dec. 17, 2009, seven pages.

* cited by examiner

*Primary Examiner* — Patrick Lewis
(74) *Attorney, Agent, or Firm* — Rankin, Hill & Clark LLP

(57) ABSTRACT

Water-soluble iron-carbohydrate derivative complex obtainable from an aqueous iron(III) salt solution and an aqueous solution of the product of the oxidation and subsequent derivative of one or more maltodextrins with an aqueous hypochlorite solution at an alkaline pH value, wherein when one maltodextrin is used its dextrose equivalent is from 5 to 20 and when a mixture of a plurality of maltodextrins is used the dextrose equivalent of the mixture is from 5 to 20 and the dextrose equivalent of each individual maltodextrin in the mixture is from 2 to 40, and the subsequent derivative is carried out with a suitable reagent, process for the preparation thereof, and medicament for the treatment and prophylaxis of iron deficiency states.

16 Claims, No Drawings

WATER-SOLUBLE IRON CARBOHYDRATE DERIVATIVE COMPLEXES, THE PREPARATION THEREOF, AND MEDICAMENTS COMPRISING THEM

The present invention provides water-soluble iron-carbohydrate derivative complexes which are suitable for the therapy of iron deficiency states, and the preparation thereof, medicaments comprising them, and the use thereof in the prophylaxis or therapy of iron deficiency states. The medicaments are suitable in particular for parenteral administration.

Anaemias caused by iron deficiency can be treated or treated prophylactically by administration of medicaments containing iron. The use of iron-carbohydrate complexes is known for this purpose. A preparation that is frequently used successfully in practice is based on a water-soluble iron(III) hydroxide-saccharose complex (Danielson, Salmonson, Derendorf, Geisser, Drug Res., Vol. 46: 615-621, 1996). Iron-dextran complexes as well as complexes based on poorly obtainable pullulans (WO 02/46241), which have to be prepared under pressure at high temperatures and with the involvement of hydrogenation steps, are also described in the prior art for parenteral administration. Further iron-carbohydrate complexes are conventional for oral administration.

WO 2004/037865 in the name of the applicants discloses an iron preparation which is preferably administrable parenterally and which can be sterilised comparatively simply; the previously known parenterally administrable preparations based on saccharose or dextran were stable only at temperatures up to 100° C., which made sterilisation difficult. The preparation has reduced toxicity and involves a reduced risk of dangerous anaphylactic shocks inducible by dextran. The high stability of the complex permits a high administration dose or a high administration rate. The iron preparation can be produced from readily obtainable starting materials without any particular outlay. There are disclosed in particular water-soluble iron(III)-carbohydrate complexes based on the oxidation products of maltodextrins, and a process for the preparation thereof. These iron(III)-carbohydrate complexes are obtainable from an aqueous iron(III) salt solution and an aqueous solution of the product of the oxidation of one or more maltodextrins with an aqueous hypochlorite solution at an alkaline pH value of, for example, from 8 to 12, wherein when one maltodextrin is used its dextrose equivalent is from 5 to 20 and when a mixture of a plurality of maltodextrins is used the dextrose equivalent of the mixture is from 5 to 20 and the dextrose equivalent of the individual maltodextrins in the mixture is from 2 to 40.

T. Nakano et al., Nahrung/Food 47 (2002) No. 4, p. 274-278 describe a process for the phosphorylation of inter alia dextrin by dry heating in the presence of phosphate. Degrees of phosphorylation of the dextrin of 1.07%, 2.42% and 3.2% are mentioned, which are obtained in dependence on the temperature and moisture content of the dextrin. The resulting phosphorylated product is tested for its ability to solubilise phosphate. The possibility of replacing casein phosphopeptide as calcium phosphate absorption increasing agent by phosphorylated dextrin is discussed.

Further possible synthesis methods for phosphorylated dextrins are also mentioned in the mentioned document, in particular drying with a phosphate-containing solution or dry phosphorylation with orthophosphate, with heating and in vacuo.

M. Z. Sitohy et al., Starch/Stärke 53 (2001), 317-322 describe the phosphorylation of starch by mixing with a solution of monosodium and disodium phosphate, filtering off, drying, pulverisation and subsequent heating. The phosphorylated product is tested for its hydrolytic stability during acidic and enzymatic hydrolysis, and the use thereof in admixture with polyacrylate and urea in biodegradable plastics is proposed.

U.S. Pat. No. 4,841,040 describes the preparation of phosphorylated dextrins having a molecular weight of from 1500 to 40,000 daltons and a degree of substitution of from 0.30 to 0.96 and their use as dispersing agents for aqueous suspensions of minerals and inorganic pigments having a high solids content, as a replacement for gum arabic in gumming and ink solutions for lithography, and as a drilling fluid additive. The degree of substitution is thereby defined by the molar ratio of the derivatised anhydroglucose units to the total amount of anhydroglucose units within a molecule. This is referred to hereinbelow as the degree of molar substitution (MS). The phosphorylated dextrins are obtained by oxidation and depolymerisation of starch by reaction with sodium hypochlorite in alkaline medium and subsequent or prior phosphorylation, for example with phosphoric acid, phosphorus pentachloride, phosphoryl chloride or polymeric sodium orthophosphates, in particular sodium trimetaphosphate.

CH-544 779 describes a process for the preparation of phosphorylated dextrins by heating a mixture of starch and a phosphoric acid solution at a pH of less than 5, with a reduced oxygen content, and then further heating in a second stage, with an even lower oxygen content, until the phosphorus compound is condensed with the starch product, and subsequent cooling with a reduced oxygen content. The resulting dextrin phosphate has very high water solubility. Its usability as a surface size for papers and in the production of adhesives is likewise mentioned.

WO 2006/082043 describes in the introduction some processes for the preparation of starch phosphates, for example according to the Neukom process (U.S. Pat. No. 2,884,412) by suspension in an aqueous alkali phosphate solution, filtration, drying and tempering at temperatures of about 140° C., in a homogeneous process using tetrapolyphosphoric acid in the presence of tributylamine in dimethylformamide (Towle et al., Methods Carbohydr. Chem. 6, (1972), 408-410) or heterogeneously in a slurry process in benzene with phosphoric anhydride (Tomasik et al., Starch/Stärke 43 (1991), 66-69). The document itself proposes a process for the preparation of highly substituted starch phosphates, in which starch is dissolved in a mixture of phosphating agent (in particular phosphate salts or urea phosphate) and water and, if the phosphating agent is free of urea, urea, the water is removed, and then a thermal reaction to give starch phosphate takes place. The resulting starch phosphate has a degree of substitution of phosphate groups of from 0.01 to 2.0 and a very low content of carbamate groups. The use of the resulting starch phosphates as an additive in mineral or dispersion-bonded building material systems, as an additive in pharmacy and cosmetics, as an anionic component for polyelectrolyte complexes and as a carrier material is proposed.

U.S. Pat. No. 3,732,207 discloses the preparation of dextrin esters using organic dibasic acid anhydrides, in particular succinic anhydride or maleic anhydride, by heating starch or dextrin having a residual moisture content of about 3% in the presence of the organic acid anhydride in an acidic environment. A dextrin ester having a degree of molar substitution of from 0.02 to 0.04 is obtained.

U.S. Pat. No. 4,100,342 describes the preparation of dextrin esters by reaction of dextrin with acid anhydrides of non-aromatic carboxylic acids having from 2 to 4 carboxylic acid units in acetic acid in the presence of a tertiary amine as catalyst, and the use of the resulting dextrin esters as biodegradable components for increasing the cleaning action of detergents.

WO 2004/064850 and WO 92/04904 disclose dextrin sulfates and their use, either alone or in combination with a bacteriostatic agent, as an antiviral composition, in particular for the treatment of HIV and other sexually transmittable diseases. The dextrin sulfates having a degree of substitution of up to 2 sulfate groups per glucose unit are prepared by hydrolysis of starch and subsequent sulfation. Trimethylamine/sulfur trioxide complex in an aqueous alkaline medium yields mainly the 2-sulfate, cyclamic acid in dimethylformamide yields the 6-sulfate, and acetylation, subsequent sulfation with trimethylamine/sulfur trioxide complex in dimethylformamide, and finally removal of the acetyl group with aqueous sodium hydroxide yield the 3-sulfate. The action of the dextrin sulfates against HIV and their antilipidaemic action are likewise disclosed in these documents.

However, none of the mentioned documents describes the formation of iron complexes with the resulting dextrin derivatives.

The object of the present invention is, therefore, to provide novel iron-carbohydrate complexes which are suitable for the treatment of iron deficiency anaemia.

The object is achieved by the complexes according to claim 1. Preferred forms of the complexes are defined in claims 2 and 3.

The complexes according to the invention are obtained by the process defined in claims 4 to 10.

Maltodextrins are used as starting material according to the invention. These are readily obtainable starting materials which are available commercially.

For the preparation of the ligands of the complexes according to the invention, the maltodextrins are first oxidised in aqueous solution with hypochlorite solution. This process is already described in WO 2004/037865, the totality of the disclosure of which is incorporated by reference herein.

There are suitable, for example, solutions of alkali hypochlorites, such as sodium hypochlorite solution. Commercial solutions can be used. The concentrations of the hypochlorite solutions are, for example, at least 13 wt. %, preferably of the order of magnitude of from 14 to 16 wt. %, in each case calculated as active chlorine. The solutions are preferably used in an amount such that approximately from 80 to 100%, preferably approximately 90%, of an aldehyde group is oxidised per maltodextrin molecule. In this manner, the reducing power determined by the glucose contents of the maltodextrin molecules is reduced to approximately 20% or less, preferably to 10% or less.

The oxidation takes place in alkaline solution, for example a pH values of from 8 to 12, for example from 9 to 11. For the oxidation it is possible to work, for example, at temperatures of the order of magnitude of from 15 to 40° C., preferably from 20 to 35° C. The reaction times are, for example, of the order of magnitude of from 10 minutes to 4 hours, for example from 1 to 1.5 hours.

By means of the described procedure, the degree of depolymerisation of the maltodextrins used is kept low. Without giving a binding theory, it is assumed that the oxidation takes place predominantly at the terminal aldehyde group (or semi-acetal group) of the maltodextrin molecules. For the sake of simplicity, this synthesis step is referred to hereinbelow as "$C_1$ oxidation", but this term is not intended to be binding.

It is also possible to catalyse the oxidation reaction of the maltodextrins. The addition of bromide ions, for example in the form of alkali bromides, for example sodium bromide, is suitable for this purpose. The amount of bromide added is not critical. It is kept as small as possible in order to obtain an end product (Fe complex) that is as simple to purify as possible. Catalytic amounts are sufficient. As mentioned, the addition of bromide is possible but not necessary.

In addition, it is also possible, for example, to use the known ternary oxidation system hypochlorite/alkali bromide/2,2,6,6-tetramethylpiperidin-1-oxyl (TEMPO) for the oxidation of the maltodextrins. The procedure of oxidising maltodextrins with alkali bromide catalysis or using the ternary TEMPO system is described, for example, by Thaburet et al. in Carbohydrate Research 330 (2001) 21-29; the procedure described therein can be used according to the invention.

Working up and isolation of the oxidised maltodextrins are carried out by adjusting the reaction solution to an approximately neutral pH by means of suitable acids or buffers, such as, for example, hydrochloric acid, sulfuric acid or acetic acid.

The oxidised reaction product can then be precipitated by addition of a suitable solvent in which it is substantially insoluble. An example of a suitable solvent is ethanol, which is preferably used in a concentration of from 80 to 95 wt. %, particularly preferably from 90 to 94 wt. %, in a volume ratio ethanol:reaction solution of approximately from 1:5 to 1:10, preferably from 1:5 to 1:8. Further suitable precipitation solvents are methanol, propanol or acetone. The precipitate is then filtered off and dried in a conventional manner.

Alternatively, the reaction solution can be purified by means of dialysis or membrane filtration and the product can be obtained by lyophilisation or spray drying.

It is also possible, however, to use the $C_1$-oxidised maltodextrin directly in the subsequent derivatisation step without isolating it.

The subsequent derivatisation of the resulting $C_1$-oxidised products takes place by conventional processes, known to the person skilled in the art, for the derivatisation of sugars, for example by oxidation, esterification with mono- or polyfunctional inorganic or organic acids or acid derivatives, carboxyalkylation, addition of organic isocyanates, etherification, amidation, anhydride formation, etc.

For example, an esterification can be carried out with organic acids or acid derivatives. Any carboxylic acids or reactive carboxylic acid derivatives known to the person skilled in the art can be used for the esterification, preferably acid chlorides, anhydrides or bromides. $C_1$-$C_6$-Carboxylic acid derivatives are preferably used for the esterification, particularly preferably acetic anhydride. The esterification is carried out under conventional reaction conditions, for example in aqueous solution or in a suitable solvent such as, for example, formamide, dimethylformamide, dimethyl sulfoxide or acetic acid. The reaction in aqueous solution can take place, for example, at a slightly basic pH of approximately from 7.5 to 10, preferably from 8 to 9.5 (the pH can be adjusted and kept constant during the reaction using any desired bases, for example alkali or alkaline earth hydroxides such as sodium or potassium hydroxide as well as alkali or alkaline earth carbonates) by addition of the reactive carboxylic acid derivative, for example acetyl chloride or acetic anhydride. When a different solvent is used, the same reagents are employed and suitable reaction conditions are chosen. The reaction can take place in the mentioned solvents at room temperature, with cooling or with heating. The reaction time is, for example, from 0.5 to 2 hours, preferably from 0.75 to 1.5 hours. Working up is carried out as described for the $C_1$ oxidation by precipitation, filtering off and drying.

An esterification with polybasic organic carboxylic acids can also take place in the same manner, for example the preparation of succinic acid, maleic acid, fumaric acid, glutaric acid or adipic acid esters, it being possible for the second carboxyl group of the ester either to be free or to be in the form of the alkyl ester. The anhydrides, mixed anhydrides, chlorides or bromides or other reactive derivatives of the polybasic carboxylic acids are suitable for the preparation, for example in particular succinic anhydride, maleic anhydride, glutaric anhydride, adipic anhydride or fumaric acid dichloride. The reaction and working up are carried out as described for the esterification. Particular preference is given to esterification with succinic anhydride to give succinyl maltodextrin.

The $C_1$-oxidised maltodextrins can likewise be reacted to give carboxyalkyl derivatives. Suitable as reagent are carboxyalkyl halides known to the person skilled in the art, for example halocarboxylic acids such as chloro- or bromo-carboxylic acids or their sodium or potassium salts, for example $C_1$-$C_6$-carboxylic acids halogenated in any desired position, such as, for example, α- or β-bromopropionic acid or, particularly preferably, chloro- or bromo-acetic acid.

The reaction is carried out in a manner known to the person skilled in the art, for example in aqueous solution or in a suitable solvent such as, for example, formamide, dimethylformamide, dimethyl sulfoxide or acetic acid. In aqueous solution, the reaction is carried out, for example, at a basic pH (pH 11 to 14, preferably approximately 12.5 to 14, adjustment using any desired bases, e.g. NaOH). When a different solvent is used, the same reagents are employed and suitable reaction conditions are chosen. The reaction can take place in the mentioned solvents at room temperature, with cooling or with heating for, for example, from 0.5 to 5 hours, preferably approximately from 2.5 to 3.5 hours. Working up and isolation are carried out as described for the esterification.

The esterification with reactive derivatives of inorganic acids, for example the sulfation or phosphation, likewise take place by processes known to the person skilled in the art.

The sulfation is carried out, for example, in aqueous solution or in a suitable solvent such as, for example, formamide, dimethylformamide, dimethyl sulfoxide or acetic acid, using a suitable sulfation reagent, for example $SO_3$-trimethylamine complex or cyclamic acid, at room temperature, with cooling or with heating, preferably, for example, at 30° C. for a suitable time, for example from 15 minutes to 2 hours, preferably for approximately 30 minutes. Then, when water is used as solvent, the pH of the reaction solution is rendered strongly basic (e.g. to pH 12-13) and the solution is stirred further at a suitable temperature, for example at 30° C. After acidification to pH 9.5 to 11, preferably approximately 10.5, using a suitable acid or a buffer, such as, for example, HCl, precipitation and isolation are carried out as described for the $C_1$ oxidation.

The phosphation is carried out according to any process known to those skilled in the art. One possibility comprises dissolving dextrin in water with the phosphating reagent and establishing a pH value of from 2 to 6, preferably approximately 3. Suitable phosphating reagents are any known reagents, a mixture of sodium dihydrogen phosphate/disodium hydrogen phosphate in a molar ratio of from 1:0.5 to 1:2.5, for example 1:1.8, preferably being used. The reaction solution can be precipitated with ethanol, methanol or acetone, for example, and the precipitate can be isolated and dried, or the reaction solution is concentrated to dryness by evaporation, for example in a rotary evaporator, and dried further, preferably at elevated temperature and in vacuo. After grinding, the product is heated in the dry state, for example to from 120 to 180° C., preferably from 150 to 170° C., preferably in vacuo, and ground again and subsequently dissolved in water or a suitable solvent, preferably at an elevated temperature of, for example, 50° C. Insoluble residues are then separated off, for example by centrifugation or filtration, and the resulting solution is purified by membrane filtration in order to remove free orthophosphate. The filtration can be monitored by IR spectroscopy or conductivity measurement. When all the orthophosphate has been removed, the solution is concentrated using a rotary evaporator and then precipitated and isolated as described for the esterification.

$C_2$/$C_3$-Oxidised derivatives can be obtained by oxidation, known to the person skilled in the art, of the $C_1$-oxidised maltodextrin with a suitable oxidising agent such as, for example, NaOCl or $NaIO_4$/$NaOCl_2$. The oxidation is carried out, for example, in aqueous solution or in a suitable solvent such as dimethylformamide, formamide, dimethyl sulfoxide or acetic acid, at room temperature, with heating or with cooling. When water is used as solvent, the reaction takes place at a slightly basic, constant pH of from 7.5 to 9.5, preferably from 8.5 to 9.0, for example by sodium hypochlorite at approximately 50° C. The pH is then adjusted to neutral, for example by addition of HCl, and the product is subsequently precipitated and isolated as described for the esterification.

By using different amounts of the respective reagents for the derivatisation, different degrees of molar substitution can be achieved. The degree of molar substitution is defined by the molar ratio of the derivatised anhydroglucose units to the total amount of anhydroglucose units within a molecule.

The products are investigated by IR spectroscopy. In this manner it is possible to determine qualitatively whether the desired functional group has been introduced into the maltodextrin. The introduction of a carboxyl group, for example of an acetyl group, succinyl group or carboxymethyl group, can be monitored by augmentation of the band at 1740 cm$^{-1}$ in the IR spectrum (C=O valence vibration of COOR). The successful $C_2$/$C_3$ oxidation can be monitored by augmentation of the band at 1640 cm$^{-1}$ (C=O valence vibration of COO$^-$). The introduction of a sulfate group can be confirmed by increase of the bands at 1260 and 830 cm$^{-1}$ (valence vibrations of $SO_4^{2-}$). The introduction of a phosphate group can also be confirmed qualitatively by $^{31}$P-NMR spectroscopy. Polymer-bound monophosphate appears in the form of broad signals at about 0 to 2 ppm, while free monophosphate shows a sharp signal at about 0.7 ppm.

The quantitative determination of the degree of molar substitution can be carried out by $^1$H-NMR spectroscopy or $^{13}$C-NMR spectroscopy, by relating the intensity of a signal assigned to the introduced functional group to the intensity of a signal of the maltodextrin that has not been influenced by the derivatisation. In the case of phosphation, the quantitative determination of the degree of molar substitution can also be carried out by ICP-OES (Inductively Coupled Plasma-Optical Emission Spectroscopy, total phosphate content) and ion chromatography coupled with conductivity measurement (content of free monophosphate).

For the preparation of the complexes according to the invention, the resulting oxidised derivatised maltodextrins are reacted in aqueous solution with an iron(III) salt. To this end, the oxidised derivatised maltodextrins can be isolated and dissolved again; the resulting aqueous solutions of the oxidised derivatised maltodextrins can, however, also be used directly for further processing with aqueous iron(III) solutions.

As iron(III) salts there can be used water-soluble salts of inorganic or organic acids or mixtures thereof, such as halides, for example chloride and bromide, or sulfates. Physiologically acceptable salts are preferably used. An aqueous solution of iron(III) chloride is particularly preferably used.

It has been shown that the presence of chloride ions has an advantageous effect on the complex formation. Chloride ions can be added, for example, in the form of water-soluble chlorides, such as alkali metal chlorides, e.g. sodium chloride, potassium chloride or ammonium chloride. Preference is given, as mentioned, to the use of iron(III) in the form of the chloride.

For the reaction, it is possible, for example, to mix the aqueous solution of the oxidised maltodextrin with an aqueous solution of the iron(III) salt. The procedure thereby is preferably such that the pH value of the mixture of oxidised maltodextrin and iron(III) salt during and immediately after mixing is initially strongly acidic or is sufficiently low that hydrolysis of the iron(III) salt does not occur, for example 2 or less, in order to avoid undesirable precipitation of iron hydroxides. When iron(III) chloride is used, it is generally not necessary to add an acid because aqueous solutions of iron (III) chloride can themselves be sufficiently acidic. When mixing has taken place, the pH value can be raised, for example, to values of the order of magnitude of equal to or greater than 5, for example up to 11, 12, 13 or 14. Raising of the pH value is preferably carried out slowly or gradually, which can be effected, for example, by first adding a weak base, for example to a pH of approximately 3; further neutralisation can then take place using a stronger base. Suitable weak bases are, for example, alkali or alkaline earth carbonates, bicarbonates, such as sodium and potassium carbonate or bicarbonate, or ammonia. Strong bases are, for example, alkali or alkaline earth hydroxides, such as sodium, potassium, calcium or magnesium hydroxide.

The reaction can be furthered by heating. For example, temperatures of the order of magnitude of from 15° C. to the boiling temperature can be applied. It is preferred to increase the temperature gradually. For example, heating can be carried out first to approximately from 15 to 70° C. and then the temperature can be gradually increased to boiling.

The reaction times are, for example, of the order of magnitude of from 15 minutes to several hours, e.g. from 20 minutes to 4 hours, for example from 25 to 70 minutes, e.g. from 30 to 60 minutes.

The reaction can take place in the weakly acidic range, for example at pH values of the order of magnitude of from 5 to 6. It has been shown, however, that it is advantageous, although not necessary, to raise the pH value to higher values, up to 11, 12, 13 or 14, in the course of the complex formation. In order to complete the reaction, the pH value can then be lowered further, for example to the mentioned order of magnitude of from 5 to 6, by the addition of an acid. As acids there can be used inorganic or organic acids or mixtures thereof, in particular hydrohalic acids, such as hydrogen chloride or aqueous hydrochloric acid.

As mentioned, the complex formation is generally furthered by heating. For example, in the preferred embodiment in which the pH value is increased in the course of the reaction to ranges of from beyond 5 to 11 or 14, it is possible first to work at low temperatures of the order of magnitude of from 15 to 70° C., for example from 40 to 60° C., e.g. at approximately 50° C., whereupon, after again lowering the pH value to values of, for example, the order of magnitude of at least 5, gradual heating is carried out to temperatures of from above 50° C. to the boiling temperature.

The reaction times are of the order of magnitude of from 15 minutes to several hours and can vary according to the reaction temperature. When the process is carried out with the temporary application of pH values that are above 5, it is possible to work at the elevated pH value for from 15 to 70 minutes, for example, e.g. for from 30 to 60 minutes, for example at temperatures up to 70° C., whereupon, after lowering the pH value to the range of the order of magnitude of at least 5, the reaction can be carried out for a further 15 to 70 minutes, e.g. 30 to 60 minutes, at temperatures of up to, for example, 70° C. and optionally for a further 15 to 70 minutes, e.g. 30 to 60 minutes, at higher temperatures up to the boiling point.

When the reaction has been carried out, the resulting solution can, for example, be cooled to room temperature and optionally diluted and optionally filtered. After cooling, the pH value can be adjusted to the neutral point or slightly below, for example to values of from 5 to 7, by addition of acid or base. There can be used as acids or bases, for example, those mentioned above for the reaction. The resulting solutions are purified and can be used directly for the preparation of medicaments. However, it is also possible to isolate the iron(III) complexes from the solution, for example by precipitation with an alcohol, such as an alkanol, for example ethanol. The isolation can also be carried out by spray drying. Purification can be carried out in a conventional manner, in particular in order to remove salts. This can be effected, for example, by reverse osmosis, it being possible for such a reverse osmosis to be carried out, for example, before the spray drying or before the direct use in medicaments.

The resulting iron(III)-carbohydrate complexes have, for example, an iron content of from 10 to 40% wt./wt., in particular from 20 to 35% wt./wt. They are readily soluble in water. It is possible to prepare therefrom neutral aqueous solutions having an iron content of, for example, from 1% wt./vol. to 20% wt./vol. Such solutions can be sterilised by means of heat. The weight-average molecular weight Mw of the complexes so obtained is, for example, from 80 kDa to 800 kDa, preferably from 80 to 650 kDa, particularly preferably up to 350 kDa (determined by means of gel permeation chromatography, for example as described by Geisser et al. in Arzneim. Forsch/Drug Res. 42(11), 12, 1439-1452 (1992), Section 2.2.5.).

As mentioned, aqueous solutions can be prepared from the complexes according to the invention. Such solutions are suitable in particular for parenteral administration. However, they can also be administered orally or topically. They can be sterilised at high temperatures, e.g. at 121° C. and above, with short contact times of at least 15 minutes with achievement of $F_0 \geq 15$. $F_0$ is the treatment time in minutes at a variable temperature that corresponds to the treatment time in minutes at 121° C. calculated for an ideal microorganism having a temperature coefficient of microbial decomposition of 10. Preparations known hitherto had in some cases to be sterile filtered at room temperature and/or have preservatives, such as benzyl alcohol or phenol, added thereto. Such working steps or additives are not necessary according to the invention. It is possible to introduce the solutions of the complexes into ampoules, for example. For example, solutions of from 1 to 20 wt. %, for example 5 wt. %, can be introduced into vessels, such as ampoules or vials, of, for example, from 2 to 100 ml, for example up to 50 ml. The preparation of the parenterally administrable solutions can be carried out in a conventional manner, optionally with the concomitant use of additives conventional for parenteral solutions. The solutions can be so formulated that they can be administered as such by injection or as an infusion, for example in saline solution. For oral or topical administration, preparations can be formulated with appropriate conventional excipients and auxiliary substances.

The invention therefore further provides medicaments which are suitable in particular for parenteral, intravenous as well as intramuscular administration and also for oral or topical administration, and which can be used in particular for the treatment of iron deficiency anaemias. The invention therefore further provides the use of the iron(III)-carbohydrate derivative complexes according to the invention in the treatment and prophylaxis of iron deficiency anaemias or in the preparation of medicaments for in particular the parenteral treatment of iron deficiency anaemias. The medicaments are suitable for use in human and veterinary medicine.

According to the invention it is possible for the first time to prepare iron complexes of maltodextrin derivatives.

Compared with the iron-maltodextrin complexes known from WO 2004/037865, the iron-maltodextrin derivative complexes according to the invention permit a specific and fine adjustment of the molecular weight over a wide range to higher molecular weights, which was not possible with the known complexes.

The majority of the iron-maltodextrin derivative complexes exhibit a virtually unchanged degradation kinetics ($\Theta$=0.5) as compared with the iron-maltodextrin complexes known from WO 2004/037865.

Most derivatised maltodextrin ligands exhibit increased stability towards enzymatic degradation by amylase as compared with underivatised maltodextrin, which can promote retarded and uniform degradation of the iron-maltodextrin derivative complexes according to the invention in the body.

The iron yields of the complex derivatives according to the invention reach 100% (in particular in the case of the sulfated complex derivatives), as compared with 87 to 93% in the known iron-maltodextrin complexes, which represents an economic advantage for production on a commercial scale.

EXAMPLES

In the present description and the examples which follow, dextrose equivalents are determined gravimetrically. To this end, the maltodextrins are reacted in aqueous solution with Fehling's solution, at boiling. The reaction takes place quantitatively, i.e. until no further discolouration of the Fehling's solution occurs. The precipitated copper(I) oxide is dried to a constant weight at 105° C. and determined gravimetrically. The glucose content (dextrose equivalent) is calculated from the resulting values as % wt./wt. of maltodextrin dry substance. For example, it is possible to work with the following solutions: 25 ml of Fehling's solution I, mixed with 25 ml of Fehling's solution II; 10 ml of aqueous maltodextrin solution (10% mol/vol.) (Fehling's solution I: 34.6 g of copper(II) sulfate dissolved in 500 ml of water; Fehling's solution II: 173 g of potassium sodium tartrate and 50 g of sodium hydroxide, dissolved in 400 ml of water).

It is explained hereinbelow which methods and devices were used to determine the respective properties of the maltodextrin derivatives and iron complexes.

$^1$H-NMR: Bruker Avance-400, 400 MHz, solution in $D_2O$ referenced to $H_2O$ $^{13}$C-NMR: Bruker Avance-400, 100 MHz, solution in $D_2O$ referenced externally to trimethylsilyl-tetradeutero-propionic acid $^{31}$P-NMR: Bruker Avance-400, 162 MHz, solution in $D_2O$ referenced externally to conc. $H_3PO_4$ IR: FT-IR Perkin Elmer 1725x, KBr pellet ICP-OES: Horiba Jobin Yvon Ultima 2, sample dissolved in $H_2O$ IC: Metrohm 733 IC Separation Center (incl. conductivity detector), sample dissolved in $H_2O$ GPC: Waters 515 HPLC pump, Waters 2410 Refractive Index Detector, sample dissolved in $H_2O$, pullulan as standard Determination of $M_w$: see GPC Determination of $M_n$: see GPC Fe content: titrimetric determination with EDTA (e.g. Jander Jahr, Massanalyse 15th Edition)

Degradation kinetics: P. Geisser, M. Baer, E. Schaub; Structure/Histotoxicity Relationship of Parenteral Iron Preparations; Arzneim.-Forsch./Drug Research 42 (II), 12, 1439-1452 (1992)

Analysis Jena Specord 205 spectral photometer, investigated degree of degradation 50% ($\Theta$=0.5)

Iron yield: amount of Fe isolated in g/amount of Fe used in g

Example 1

Preparation of $C_1$-Oxidised Maltodextrin 250 g of maltodextrin having a dextrose equivalent of 12 were dissolved in 750 ml of water. 1.4 g of NaBr were added, and 78.4 g of NaOCl solution (14 to 16 wt. % active chlorine) were metered in the course of 30 minutes, the pH being kept constant at 9.5 (±0.5) by addition of 30 wt. % NaOH. The pH was then adjusted to 7.0 using HCl (20 wt. %), and the product was precipitated by addition of ethanol (92 wt. %) in a volume ratio of 1:6 (solution:ethanol). The product was isolated by decanting off the supernatant solution and was dried for 24 hours at 50° C. and 125 mbar.

Example 2

Preparation of $C_1$-Oxidised Maltodextrin 100 g of maltodextrin (9.6 dextrose equivalents, determined gravimetrically) are dissolved at 25° C., with stirring, in 300 ml of water and oxidised at pH 10 by addition of 30 g of sodium hypochlorite solution (14 to 16 wt. % active chlorine) and isolated and dried as in Example 1.

Example 3

Preparation of $C_1$-Oxidised Maltodextrin

A mixture of 45 g of maltodextrin (6.6 dextrose equivalents, determined gravimetrically) and 45 g of maltodextrin (14.0 dextrose equivalents, determined gravimetrically) is dissolved at 25° C., with stirring, in 300 ml of water and oxidised at pH 10 by addition of 25 g of sodium hypochlorite solution (14 to 16 wt. % active chlorine) and isolated and dried as in Example 1.

Examples 4 to 7

Acetylation 200 g of maltodextrin obtained in Example 1 (1.23 mol of anhydroglucose) were dissolved at 25° C. in 660 ml of water, and the pH was adjusted to 8.5 using 30 wt. % NaOH. Acetic anhydride was added at a rate of 1.7 ml/min. in various amounts shown in Table 1, the pH being kept constant at 8.5 (±0.5) by addition of 30 wt. % NaOH. The solution was stirred for one hour at a constant pH of 8.5 (±0.5) and then adjusted to 7.0 using 20 wt. % HCl. The product was precipitated with ethanol (92 wt. %) in a volume ratio of 1:6 (solution:ethanol). The product was isolated by decanting off the supernatant solution and was dried for 24 hours at 50° C. and 125 mbar.

By varying the amount of added acetic anhydride, different degrees of acetylation were obtained. The results are shown in Table 1.

TABLE 1

| Example | Equivalents of $Ac_2O$ (based on anhydroglucose) | Degree of molar substitution ($^1$H-NMR) | Yield [%] (mol of isolated product/mol of anhydroglucose used) |
|---|---|---|---|
| 4 | 1 | 0.84 | 24 |
| 5 | 0.67 | 0.61 | 65 |
| 6 | 0.33 | 0.31 | 69 |
| 7 | 0.16 | 0.14 | 74 |
| 1 | — | not derivatised | 84 |

Owing to the acetylation, the solubility of the maltodextrin derivative in ethanol increases, which results in a falling yield with an increasing degree of substitution.

The degree of acetylation was determined qualitatively by IR spectroscopy and quantitatively by NMR spectroscopy.

The acetylation can be monitored by IR spectroscopy by augmentation of the band at 1740 cm$^{-1}$ (C=O valence vibration of COOR). The degree of molar acetylation was determined by $^1$H-NMR spectroscopy by the ratio of the intensity of the $CH_3$ signal at 2.0-2.3 ppm (acetyl group) to the intensity of the signal at 3.0-4.5 ppm and 5-6 ppm (7 protons of the anhydroglucose group).

Examples 8 to 11

Succinylation 200 g of $C_1$-oxidised maltodextrin obtained in Example 1 were dissolved in 655 ml of water. The pH was adjusted to 8.5 using 30 wt. % NaOH, and succinic anhydride was added in portions at 25° C. in the course of one hour, the pH being kept constant at 8.5 (±0.5) by addition of 30 wt. % NaOH. The pH was then adjusted to 7.0 by addition of 20 wt. % HCl and the product was precipitated with ethanol (92 wt. %) in a volume ratio solution:ethanol of 1:6. The product was isolated by decanting off the supernatant solution and was dried for 24 hours at 50° C. and 125 mbar.

By varying the added amount of succinic anhydride, different degrees of succinylation were obtained. The results are shown in Table 2.

TABLE 2

| Example | Equivalents of succinic anhydride (based on anhydroglucose) | Degree of molar substitution ($^1$H-NMR) | Yield [%] (mol of isolated product/mol of anhydroglucose used) |
|---|---|---|---|
| 8 | 0.17 | 0.15 | 74 |
| 9 | 0.08 | 0.07 | 82 |
| 10 | 0.04 | 0.03 | 84 |
| 11 | 0.02 | 0.02 | 70 |
| 1 | — | not derivatised | 84 |

The succinylation did not significantly affect the solubility of the oxidised maltodextrin.

The succinylation can be monitored qualitatively by IR spectroscopy by augmentation of the band at 1740 cm$^{-1}$ (C=O valence vibration of COOR/COOH). The degree of molar succinylation was determined by $^1$H-NMR spectroscopy by the ratio of the intensity of the two $CH_2$ signals at 2.4-2.7 ppm (succinyl group) to the intensity of the signal at 3.0-4.5 ppm and 5-6 ppm (7 protons of the anhydroglucose group).

Examples 12 to 16

Carboxymethylation 200 g of $C_1$-oxidised maltodextrin obtained in Example 1 were dissolved in 660 ml of water. 118 g of solid NaOH were added so that the pH was 13-14. Chloroacetic acid was added in portions in the course of 20 minutes, and then stirring was carried out at 25° C. for 3 hours. The pH was then adjusted to 7.0 by addition of 20 wt. % HCl, and the product was precipitated with ethanol (92 wt. %) in a volume ratio solution:ethanol of 1:6. The product was isolated by decanting off the supernatant solution and was dried for 24 hours at 50° C. and 125 mbar.

By varying the added amount of chloroacetic acid, different degrees of carboxymethylation were obtained. The results are shown in Table 3.

TABLE 3

| Example | Equivalents of chloroacetic acid (based on anhydroglucose) | Degree of molar substitution ($^1$H-NMR) | Yield [%] (mol of isolated product/mol of anhydroglucose used) |
|---|---|---|---|
| 12 | 0.35 | 0.034 | 63 |
| 13 | 0.23 | 0.024 | 63 |
| 14 | 0.18 | 0.017 | 76 |
| 15 | 0.09 | 0.014 | 64 |
| 16 | 0.05 | 0.008 | 63 |
| 1 | — | not derivatised | 84 |

The degrees of carboxymethylation achieved did not significantly affect the solubility of the oxidised maltodextrin.

It is not possible to monitor the carboxymethylation by IR spectroscopy because of the low degrees of substitution in these examples. (No clear band at 1740 cm$^{-1}$ of the C=O valence vibration.) The degree of molar carboxymethylation was determined by $^1$H-NMR spectroscopy by the ratio of the intensity of the anomeric protons at 5.6 ppm (carboxymethylated anhydroglucose group) to the intensity of the signal of the anomeric protons at 4.8-5.8 ppm (anhydroglucose group without derivatisation).

Examples 17 to 20

Sulfation 200 g of $C_1$-oxidised maltodextrin obtained in Example 1 were dissolved in 600 ml of water and heated to 30° C. $SO_3$-trimethylamine complex was added and the mixture was stirred at 30° C. for 30 minutes (during which the suspension changed into a solution). 40 wt. % NaOH (1.7 equivalents, based on the molar amount of $SO_3$-trimethylamine complex, corresponding to 18-141 ml depending on the degree of substitution) were added at a rate of 2.8 ml/min., and the solution was stirred at 30° C. for 2.5 hours. The pH was adjusted to 10.5 with 20 wt. % HCl. The product was precipitated with 92 wt. % ethanol in a volume ratio solution:ethanol of 1:7 to 1:8. The product was isolated by decanting off the supernatant solution and was dried for 24 hours at 50° C. and 125 mbar.

By varying the added amount of $SO_3$-triethylamine complex, different degrees of sulfation were obtained. The results are shown in Table 4.

TABLE 4

| Example | Equivalents of SO$_3$ reagent (based on anhydroglucose) | Degree of molar substitution ($^1$H-NMR) | Yield [%] (mol of isolated product/mol of anhydroglucose used) |
|---|---|---|---|
| 17 | 0.67 | 0.56 | 98 |
| 18 | 0.34 | 0.27 | 92 |
| 19 | 0.17 | 0.12 | 93 |
| 20 | 0.08 | 0.05 | 86 |
| 1 | — | not derivatised | 84 |

The reason for the increasing yield of oxidised sulfated maltodextrin is the decreasing solubility of the product in ethanol.

The degree of sulfation can be monitored qualitatively by IR spectroscopy (augmentation of the bands at 1260 and 830 cm$^{-1}$, valence vibrations of SO$_4^{2-}$). The degree of molar sulfation was determined by $^{13}$C-NMR spectroscopy by the ratio of the intensity of the C$_1$ signal at 96 ppm (sulfated species) to the intensity of the C$_1$ signal at 103 ppm (non-sulfated species).

Examples 21 to 24

Phosphation 300 g of C$_1$-oxidised maltodextrin obtained in Example 1, NaH$_2$PO$_4$ and Na$_2$HPO$_4$ (molar ratio 1:1.8) were dissolved in 1.5 litres of water and the pH was adjusted to 3.0 using 20 wt. % HCl. The solution was concentrated to dryness by evaporation in a rotary evaporator at 70° C. and 125 mbar. The residue was dried for 16 hours at 50° C. and 125 mbar. This product was ground and heated to 160° C. over a period of 4 hours at 750 mbar. This material was ground again and dissolved for one hour in water in a weight ratio of 1:4.4 (solid:water) at 50° C. The solution was cooled to 25° C. and the insoluble residues were separated off by centrifugation (5500 rpm for 1 hour).

In order to remove free orthophosphate, the resulting solution was filtered by membrane filtration using a nanofiltration membrane (Nitto-Denko NTR-7410, average NaCl retention 10%) at 22 bar and a flow rate of 180-210 litres/hour. The removal of the free orthophosphate was monitored by IR spectroscopy of the washed fractions. The solution of the oxidised phosphated maltodextrin was concentrated to 1 litre in a rotary evaporator at 60° C. and 80-250 mbar, and then the product was precipitated with ethanol in a volume ratio of 1:6 (solution:ethanol). The product was separated off by centrifugation of the suspension (5500 rpm for 1 hour) and was dried for 24 hours at 50° C. and 125 mbar.

By varying the added amount of the mixture of NaH$_2$PO$_4$ and Na$_2$HPO$_4$ in a molar ratio of 1:1.8, different degrees of phosphation were obtained. The results are shown in Table 5.

The degree of molar substitution was determined by ICP-OES (Inductively Coupled Plasma-Optical Emission Spectroscopy, total phosphate content) and ion chromatography coupled with conductivity measurement (content of free monophosphate).

A qualitative determination of the content of free monophosphate was carried out by $^{31}$P-NMR spectroscopy. Polymer-bound monophosphate appears in the form of broad signals in the region of about 0-2 ppm, while free monophosphate exhibits a sharp peak at about 0.7 ppm. The broad signal at −10 ppm can be assigned to oligophosphates.

TABLE 5

| Example | Equivalents of PO$_4$ (based on anhydroglucose) | Degree of molar substitution (ICP) | Free PO$_4$ (ppm) | Free oligophosphates*** (ppm) | Yield [%] (mol of isolated product/mol of anhydroglucose used) |
|---|---|---|---|---|---|
| 21 | 1.85 | 0.25 | 80 | not determined | 22 |
| 22 | 0.55* | 0.08 | 1 | 22 | 22 |
| 23 | 0.28 | 0.24 | 2 | 55 | 13 |
| 24 | 0.23** | 0.08 | 58 | 52 | 18 |
| 1 | not derivatised | — | — | — | 84 |

*Reaction time at 160° C./740 mbar 16 hours instead of 4 hours
**The maltodextrin/phosphate solution was precipitated with ethanol instead of being concentrated to dryness by evaporation
***Content determined by $^{31}$P-NMR Examples 25 to 29

C$_2$/C$_3$ Oxidation (Two-Stage Synthesis)

200 g of C$_1$-oxidised maltodextrin obtained in Example 1 were dissolved in 600 ml of water and the solution was heated to 50° C. The pH was adjusted to 8.5 to 9.0 using 20 wt. % HCl, and 20 g of NaOCl (14 to 16% active chlorine) were added in a single batch. The residual amount of NaOCl was added at a rate of 5.8 ml/min., the pH being kept constant at 8.5 (±0.5) by addition of 30 wt. % NaOH. The solution was stirred for 1 hour at 50° C. and pH 8.5 (±0.5). The pH was then adjusted to 7 using 20 wt. % HCl. The product was precipitated with 92 wt. % ethanol in a volume ratio solution:ethanol of 1:6. The product was isolated by decanting off the supernatant solution and was dried for 24 hours at 50° C. and 125 mbar.

Example 30

C$_1$/C$_2$/C$_3$ Oxidation (Single-Stage Synthesis, In Situ Derivatisation)

200 g of maltodextrin having a dextrose equivalent of 12 were dissolved in 660 ml of water and the solution was heated to 50° C. 1.1 g of NaBr were added, and 135.2 g of NaOCl solution (14 to 16 wt. % active chlorine) were metered in in the course of 30 minutes, the pH being kept constant at 9.5 (±0.5) by addition of 30 wt. % NaOH. The solution was stirred for 1 hour at 50° C. and pH 9.5 (±0.5). The pH was then adjusted to 7 using 20 wt. % HCl. The product was precipitated with 92 wt. % ethanol in a volume ratio solution:ethanol of 1:6. The product was isolated by decanting off the supernatant solution and was dried for 24 hours at 50° C. and 125 mbar.

By varying the added amount of NaOCl (14-16% active chlorine), different degrees of molar $C_2/C_3$ oxidation were obtained. The results are shown in Table 6.

TABLE 6

| Example | Equivalents of NaOCl | Degree of molar oxidation ($^{13}$C-NMR) | Yield [%] (mol of isolated product/mol of anhydroglucose used) |
|---|---|---|---|
| 25 | 0.48 | 0.042 | 72 |
| 26 | 0.24 | 0.022 | 71 |
| 27 | 0.12 | 0.012 | 88 |
| 28 | 0.06 | not detectable | 75 |
| 29 | 0.03 | not detectable | 78 |
| 30 | 0.12 | 0.017 | 89 |
| 1 | — | not derivatised | 84 |

The variation in the isolated yield of the resulting products is small.

It was possible to monitor the degree of $C_2/C_3$ oxidation by IR spectroscopy by an augmentation of the band at 1640 cm$^{-1}$ (C=O valence vibration of COO$^-$).

The degree of molar $C_2/C_3$ oxidation was determined by $^{13}$C-NMR spectroscopy by the ratio of the intensity of the COOH signal at 175 and 176 ppm (oxidised $C_2$ and $C_3$) to the intensity of the signal at 76-84 ppm (unoxidised $C_2$).

General Process Specification 1: Preparation of Iron Complexes

The preparation of iron complexes from the resulting oxidised derivatised maltodextrins was carried out in each case using 100 g of the maltodextrin derivative:

To 352 g of iron(III) chloride solution (12% wt./wt. Fe) there were added, with stirring (paddle stirrer), at room temperature, first 100 g of the oxidised derivatised maltodextrin dissolved in 300 ml of water, and then 554 g of sodium carbonate solution (17.3% wt./wt.).

A pH of 11 was then established by addition of sodium hydroxide solution, and the solution was heated to 50° C. and maintained at 50° C. for 30 minutes. The mixture was then acidified to a pH of 5 to 6 by addition of hydrochloric acid, and the solution was maintained at 50° C. for a further 30 minutes and then heated to 97-98° C. and maintained at that temperature for 30 minutes. After cooling the solution to room temperature, the pH value was adjusted to 6-7 by addition of sodium hydroxide solution. The solution was then filtered over a sterile filter and the complex was isolated by precipitation with ethanol in a ratio of 1:0.85 and was dried in vacuo at 50° C.

Examples 31 to 33

Acetylated Iron Complexes

According to general process specification 1, the acetylated iron complexes 31 to 33 were obtained from the maltodextrin derivatives obtained in Examples 5 to 7, the properties of which are summarised in Table 7 below, in each case compared with a standard preparation which was likewise prepared according to general process specification 1 from $C_1$-oxidised but not derivatised maltodextrin as obtained in Example 1.

TABLE 7

| Parameter | Standard | Example 31 MS = 0.14 (from Example 7) | Example 32 MS = 0.31 (from Example 6) | Example 33 MS = 0.61 (from Example 5) |
|---|---|---|---|---|
| Fe content* | 27.0 | 28.9 | 29.7 | 30.6 |
| Mw | 168,000 | 234,000 | 349,000 | 511,000 |
| Mn | 100,000 | 139,000 | 163,000 | 334,000 |
| Degradation kinetics $\Theta = 0.5$ | 35 | 41 | 46 | 44 |

*Values based on dry substance

The use of acetylated maltodextrin derivatives having a degree of molar substitution >0.61 resulted in instable products.

The acetylated iron complexes exhibited increased iron contents as compared with the standard and rising molecular weights as the degree of substitution increased. The degradation kinetics at 50% showed similar values compared with the standard. The Fe yields of the acetylated iron complexes reached 97%.

Examples 34 to 36

Succinylated Iron Complexes

According to general process specification 1, the succinylated iron complexes 34 to 36 were obtained from the maltodextrin derivatives obtained in Examples 9 to 11, the properties of which are summarised in Table 8 below, in each case compared with a standard preparation which was likewise prepared according to general process specification 1 from $C_1$-oxidised but not derivatised maltodextrin as obtained in Example 1.

TABLE 8

| Parameter | Standard | Example 34 MS = 0.02 (from Example 11) | Example 35 MS = 0.03 (from Example 10) | Example 36 MS = 0.07 (from Example 9) |
|---|---|---|---|---|
| Fe content* | 27.0 | 24.3 | 26.9 | 24.4 |
| Mw | 168,000 | 260,000 | 347,000 | 773,000 |
| Mn | 100,000 | 128,000 | 145,000 | 188,000 |
| Degradation kinetics $\Theta = 0.5$ | 35 | 28 | 32 | 6 |

*Values based on dry substance

The use of succinylated maltodextrin derivatives having a degree of molar substitution >0.07 resulted in instable products.

The succinylated iron complexes exhibited slightly reduced iron contents as compared with the standard as well as rising molecular weights as the degree of substitution increased. The degradation kinetics at 50% showed similar values compared with the standard, with one exception. The Fe yields of the succinylated iron complexes reached 94%.

Examples 37 to 38

Carboxymethylated Iron Complexes

According to general process specification 1, the carboxymethylated iron complexes 37 and 38 were obtained from the maltodextrin derivatives obtained in Examples 15 to 16, the properties of which are summarised in Table 9 below, in each case compared with a standard preparation which was likewise prepared according to general process specification 1 from $C_1$-oxidised but not derivatised maltodextrin as obtained in Example 1.

TABLE 9

| Parameter | Standard | Example 37 MS < 0.01 (from Example 16) | Example 38 MS = 0.014 (from Example 15) |
|---|---|---|---|
| Fe content* | 27.0 | 23.3 | 25.5 |
| Mw | 168,000 | 316,000 | 404,000 |
| Mn | 100,000 | 148,000 | 168,000 |
| Degradation kinetics $\Theta = 0.5$ | 35 | 36 | 32 |

*Values based on dry substance

The use of carboxymethylated maltodextrin derivatives having a degree of molar substitution >0.01 resulted in instable products.

The iron contents of the carboxymethylated iron complexes were found to be slightly reduced as compared with the standard, and the molecular weights rose as the degree of substitution increased. The degradation kinetics at 50% showed almost identical values compared with the standard. The Fe yields of the carboxymethylated iron complexes reached 97%.

Examples 39 to 41

$C_2/C_3$-Oxidised Iron Complexes

According to general process specification 1, the $C_2/C_3$-oxidised iron complexes 39 to 41 were obtained from the maltodextrin derivatives obtained in Examples 27, 28 and 29, the properties of which are summarised in Table 10 below, in each case compared with a standard preparation which was likewise prepared according to general process specification 1 from $C_1$-oxidised but not derivatised maltodextrin as obtained in Example 1.

TABLE 10

| Parameter | Standard | Example 39 MS < 0.01 (from Example 29) | Example 40 MS < 0.01 (from Example 28) | Example 41 MS = 0.012 (from Example 27) |
|---|---|---|---|---|
| Fe content* | 27.0 | 22.2 | 26.1 | 23.8 |
| Mw | 168,000 | 275,000 | 310,000 | 433,000 |
| Mn | 100,000 | 138,000 | 150,000 | 230,000 |
| Degradation kinetics $\Theta = 0.5$ | 35 | 33 | 36 | 39 |

*Values based on dry substance

The use of $C_2/C_3$-oxidised maltodextrin derivatives having a degree of molar substitution >0.01 resulted in instable products.

The iron contents did not exhibit a uniform tendency, the molecular weights rose as the degree of substitution increased. The degradation kinetics at 50% showed almost identical values compared with the standard. The Fe yields of the $C_2/C_3$-oxidised iron complexes reached 95%.

Examples 42 to 44

Sulfated Iron Complexes (Multi-Stage Synthesis)

According to general process specification 1, the sulfated iron complexes 42 to 44 were obtained in multi-stage syntheses from the maltodextrin derivatives obtained in Examples 18 to 20, the properties of which are summarised in Table 11 below, in each case compared with a standard preparation which was likewise prepared according to general process specification 1 from $C_1$-oxidised but not derivatised maltodextrin as obtained in Example 1.

Example 45

Sulfated Iron Complex (Single-Stage Synthesis, In Situ Derivatisation)

100 g of maltodextrin having a dextrose equivalent of 12 were dissolved in 300 ml of water. 0.7 g of NaBr was added, and 28.7 g of NaOCl solution (14 to 16 wt. % active chlorine) were metered in the course of 30 minutes, the pH being kept constant at 9.5 (±0.5) by addition of 30 wt. % NaOH. The solution was then heated to 30° C., 14.4 g of $SO_3$-trimethylamine complex were added, and stirring was then carried out for 30 minutes at 30° C. 17.6 ml of 40 wt. % NaOH were then metered in, and stirring was carried out for 1 hour at 30° C.

After cooling the solution to 20-25° C., 352 g of iron(III) chloride solution (12% wt./wt. Fe) were added, with stirring, and then 554 g of sodium carbonate solution (17.3% wt./wt.) were metered in. A pH of 11 was then established by addition of sodium hydroxide solution, and the solution was heated to 50° C. and maintained at 50° C. for 30 minutes. The mixture was then acidified to a pH of 5 to 6 by addition of hydrochloric acid, and the solution was maintained at 50° C. for a further 30 minutes and then heated to 97-98° C. and maintained at that temperature for 30 minutes. After cooling the solution to room temperature, the pH value was adjusted to 6-7 by addition of sodium hydroxide solution. The solution was then filtered over a sterile filter and the complex was isolated by precipitation with ethanol in a ratio of 1:0.85 and was dried in vacuo at 50° C.

TABLE 11

| Parameter | Standard | Example 42 MS = 0.05 (from Example 20) | Example 43 MS = 0.12 (from Example 19) | Example 44 MS = 0.27 (from Example 18) | Example 45 MS = 0.12 |
|---|---|---|---|---|---|
| Fe content* | 27.0* | 25.3 | 26.8 | 26.3 | 26.3 |
| Mw | 168,000 | 261,000 | 278,000 | 640,000 | 160,000 |
| Mn | 100,000 | 142,000 | 219,000 | 409,000 | 106,000 |
| Degradation kinetics $\Theta = 0.5$ | 35 | 75 | 62 | 67 | — |

*Values based on dry substance

The use of sulfated maltodextrin derivatives having a degree of molar substitution >0.27 resulted in instable products.

The iron contents of the sulfated iron complexes remained almost constant as the degree of substitution increased. The molecular weights of the iron complexes synthesised in a multi-stage synthesis rose as the degree of substitution increased. The degradation kinetics at 50% showed increased values compared with the standard. The Fe yields of the sulfated iron complexes reached 100%.

The invention claimed is:

1. A water-soluble iron-carbohydrate complex obtained from the reaction of (a) an aqueous iron(III) salt solution and (b) an aqueous solution of the product of the oxidation and subsequent reaction of one or more maltodextrins, wherein the oxidation is carried out with an aqueous hypochlorite solution at a pH value in the alkaline range, wherein when one maltodextrin is used its dextrose equivalent is from 5 to 20 and when a mixture of a plurality of maltodextrins is used the dextrose equivalent of the mixture is from 5 to 20 and the dextrose equivalent of the individual maltodextrins in the mixture is from 2 to 40, and the subsequent reaction is one selected from the group consisting of
   (a) esterification with monobasic or polybasic carboxylic acid chlorides, anhydrides, mixed anhydrides or bromides (b) esterification with a sulfating reagent or a phosphating reagent, (c) oxidation of a $C_1$-oxidized maltodextrin with an oxidizing agent selected from the group consisting of NaOCl or $NaIO_4/NaOCl_2$, (d) carboxyalkylation with halogenated $C_1$-$C_6$ carboxylic acids, (e) addition of organic isocyanates, (f) etherification, (g) amidation, (h) carbamate formation, and (i) anhydride formation to form, respectively,
   (a) esters of monobasic or polybasic carboxylic acids, (b) sulfate esters or phosphate esters, (c) C2/C3 oxidation products, (d) carboxyalkylation products, (e) isocyanates, (f) ethers, (g) amides, (h) carbamates, and (i) anhydrides of inorganic acids.

2. The complex of claim 1, wherein the oxidation of the maltodextrin or maltodextrins is carried out in the presence of bromide ions.

3. The complex of claim 1, wherein the iron(III) salt is iron(III) chloride.

4. The complex of claim 1, wherein (a) the oxidized, reacted maltodextrin and (b) iron(III) salt are mixed into an aqueous solution having a pH value that is sufficiently low that hydrolysis of the iron(III) salt does not occur, whereupon the pH value is raised to from 5 to 12 by addition of base.

5. The complex of claim 4, wherein the reaction is carried out in the range of 15 minutes to several hours at a temperature in the range of 15° C. to the boiling point.

6. A medicament comprising the aqueous solution of an iron-carbohydrate complex according to claim 1.

7. The medicament of claim 6, wherein the medicament is formulated for parenteral or oral administration.

8. A process of treating iron deficiency states comprising administering to a patient in need, the iron-carbohydrate complex of claim 1.

9. A process of making a water-soluble iron-carbohydrate complex obtained from
   (a) oxidizing, at an alkaline pH in the presence of aqueous hypochlorite, one or more maltodextrins,
      wherein when one maltodextrin is used its dextrose equivalent is from 5 to 20 and when a mixture of a plurality of maltodextrins is used the dextrose equivalent of the mixture is from 5 to 20 and the dextrose equivalent of the individual maltodextrins in the mixture is from 2 to 40
   (b) subsequently reacting the one or more maltodextrins with at least one selected from the group consisting of
      (i) monobasic or polybasic carboxylic acid chlorides, anhydrides, mixed anhydrides or bromides
      (ii) inorganic sulfating reagents or inorganic phosphating reagents,
      (iii) oxidizing agents,
      (iv) halogenated $C_1$-$C_6$ carboxylic acids,
      (v) alcohols to form ethers,
      (vi) amine-group containing reagents to amides,
      (vii) carbamic acid chloride, carbamic acid bromide or carbamic anhydride to form a carbamate,
      (viii) inorganic acids to form an inorganic acid anhydrides, and
   (c) reacting the product of (b) with an aqueous iron(III) salt solution.

10. The process of claim 9, wherein the oxidation of the maltodextrin or maltodextrins is carried out in the presence of bromide ions.

11. The process of claim 9, wherein the iron(III) salt is iron(III) chloride.

12. The process of claim 9, wherein (a) oxidized reacted maltodextrin and (b) iron(III) salt are mixed into an aqueous solution having a pH value that is sufficiently low that hydrolysis of the iron(III) salt does not occur, whereupon the pH value is raised to from 5 to 12 by addition of base.

13. The process of claim 9, wherein the reaction is carried out in the range of 15 minutes to several hours at a temperature in the range of 15° C. to the boiling point.

14. A medicament comprising the aqueous solution of an iron-carbohydrate complex made according to the process of claim 9.

15. The medicament of claim 14, wherein the medicament is formulated for parenteral or oral administration.

16. A process of treating iron deficiency states comprising administering to a patient in need, the iron-carbohydrate complex made by the process of claim 9.

* * * * *